(12) United States Patent
Wang et al.

(10) Patent No.: US 8,480,635 B2
(45) Date of Patent: Jul. 9, 2013

(54) AUTOMATIC INTRAVENOUS FLUID FLOW CONTROL DEVICE

(76) Inventors: Hsien-Tsung Wang, Taipei (TW); Wan-Chang Cheng, Taipei (TW)

( * ) Notice: Subject to any disclaimer, the term of this patent is extended or adjusted under 35 U.S.C. 154(b) by 71 days.

(21) Appl. No.: 12/923,414

(22) Filed: Sep. 21, 2010

(65) Prior Publication Data

US 2011/0218501 A1    Sep. 8, 2011

(30) Foreign Application Priority Data

Mar. 4, 2010  (CN) .......................... 2010 1 0117571
Jul. 7, 2010   (CN) .......................... 2010 1 0220081

(51) Int. Cl.
*A61M 5/14*    (2006.01)
(52) U.S. Cl.
USPC .......................................................... 604/254
(58) Field of Classification Search
USPC ............... 604/7, 127, 247, 251–256; 96/158, 96/168; 137/398, 399, 429, 430, 433; 222/66, 222/67, 181.1, 444, 453, 456, 571
See application file for complete search history.

(56) References Cited

U.S. PATENT DOCUMENTS

| | | | |
|---|---|---|---|
| 2,784,733 A | * | 3/1957 | Martinez ........................ 137/399 |
| 4,678,460 A | * | 7/1987 | Rosner .......................... 604/113 |
| 6,569,116 B1 | | 5/2003 | Wang |

* cited by examiner

*Primary Examiner* — Kami A Bosworth (57) ABSTRACT

An intravenous flow control device includes a flexible drip chamber (20) comprising a fluid entrance (22) and an open bottom (231); a rigid drip assembly (30) secured to the drip chamber (20) and comprising an inner cylinder (31) having a bottom exit (331); and an internal float valve (10) comprising a fastening member (12) including a hollow inner cylinder (121), a plunger (11) slidably disposed through the inner cylinder (121), an upper float member (15) secured to one end of the plunger (11), a lower float member (13) secured to the other end of the plunger (11), and a block member (14) secured to the lower float member (13) for sealingly blocking the exit (331). Fluid flows into the inner cylinder (31) for accumulation so as to float the block member (14), thereby unblocking the exit (331) and moving the plunger (11) upward.

2 Claims, 12 Drawing Sheets

AUTOMATIC INTRAVENOUS FLUID FLOW CONTROL DEVICE

BACKGROUND OF THE INVENTION

1. Field of Invention

The invention relates to intravenous (IV) fluid flow control and more particularly to an automatic IV fluid flow control device with improved characteristics.

2. Description of Related Art

There are many devices known for controlling the flow of IV fluids to a patient. For example, U.S. Pat. No. 6,569,116 discloses an IV flow controlling device disposed in a drip chamber having an exit in a bottom, the flow controlling device comprising a flexible float member having a specific gravity less than one and an outer diameter smaller than a diameter of the drip chamber, the float member including an open upper portion and a hemi-spherical bottom portion, a wall thickness of the hemi-spherical bottom portion being thinner than a wall thickness of the upper portion of the float member, wherein the float member is submerged as fluid fills the drip chamber, fluid flowing through the exit of the drip chamber causing the float member to fall, thereby stopping fluid flowing through the exit when the flexible bottom portion of the float member blocks the exit of the drip chamber when fluid in the drip chamber is used up.

However, the prior IV flow controlling device suffers from a number of disadvantages. In detail, the device can work well when it is disposed vertically. Unfortunately, it may be inclined or may be permanently deformed due to compression. Thus, the float member may malfunction. In often times, the flexible bottom portion of the float member cannot block the exit of the drip chamber when fluid in the drip chamber is used up. Thus, the need for improvement still exists.

SUMMARY OF THE INVENTION

It is therefore one object of the invention to provide an intravenous fluid flow control device comprising a flexible drip chamber comprising a fluid entrance and an open bottom; a rigid drip assembly secured to the drip chamber and comprising an inner cylinder having a bottom exit; and a float valve disposed within both the drip chamber and the drip assembly, the float valve comprising a fastening member fastened in a joining portion of the drip chamber and the drip assembly, the fastening member including a hollow inner cylinder, an elongated plunger slidably disposed through the inner cylinder, an upper float member secured to one end of the plunger, a lower float member secured to the other end of the plunger, and a block member secured to the lower float member, the block member being for sealingly blocking the exit in an inoperative position, wherein fluid flows though the drip chamber and the fastening member into the inner cylinder for accumulation so as to float the block member, thereby unblocking the exit and moving the plunger upward.

It is another object of the invention to provide an intravenous fluid flow control device comprising a flexible drip chamber comprising a fluid entrance and an open bottom; a rigid drip assembly secured to the drip chamber and comprising an inner cylinder having a bottom exit; and a float valve disposed within both the drip chamber and the drip assembly, the float valve comprising a fastening member fastened in a joining portion of the drip chamber and the drip assembly, the fastening member including a hollow inner cylinder, an upper float member, a lower float member comprising an inner cylinder slidably passing through the inner cylinder, the inner cylinder having one end secured to the upper float member, and a block member secured to the other end of the inner cylinder, the block member being for sealingly blocking the exit in an inoperative position, wherein fluid flows though the drip chamber and the fastening member into the inner cylinder for accumulation so as to float the block member, thereby unblocking the exit and moving the lower float member upward.

In one aspect of the invention fluid may be stored in the inner cylinder to increase weight of the lower float member so as to insure the sealing engagement of the block member with the exit and thus prevent blood from flowing back to the drip assembly.

The above and other objects, features and advantages of the invention will become apparent from the following detailed description taken with the accompanying drawings.

DETAILED DESCRIPTION OF THE INVENTION

Referring to FIGS. 1 to 8, an automatic intravenous (IV) fluid flow control device in accordance with a first preferred embodiment of the invention comprises the following components as discussed in detail below.

A drip mechanism 100 is comprised of a drip chamber 20 and a drip assembly 30. A float valve 10 is provided in the drip mechanism 100. The drip chamber 20 is formed of PVC (Polyvinylchloride) or other flexible plastic material. The drip assembly 30 is formed of ABS (Acrylonitrile Butadiene Styrene) or other hard plastic material.

The drip chamber 20 comprises a reservoir 21, an inlet tube 22 at one (top) end of the reservoir 21, and a flared lower portion 23 having an open bottom 231. An inlet tubing 40 has one enlarged end 41 secured to one end of the reservoir 21. The inlet tubing 40 is in fluid communication with the reservoir 21 via the inlet tube 22. The inlet tubing 40 is connected to an IV fluid bag (not shown).

The drip assembly 30 comprises an inner cylinder 31 having a top mouth 311, an annular outer member 32 depending upward from the periphery of inner cylinder 31 to define an annular trough 321 therebetween, a hollow cylindrical extension 332 projecting from bottom center of a lower portion 33 of the inner cylinder 31, the extension 332 having an end opening 331 on the bottom of the lower portion 33 to be in fluid communication with inside of the inner cylinder 31, and a clamping connector 333 having one open end secured to the other open end of the extension 332 and the other open end secured to an open end 51 of an outlet tubing 50. The clamping connector 333 has an outlet bore less than the bore of the extension 332 so that bubbles of gas in the fluid passing the extension 332 will be squeezed to break. This can prevent bubbles of gas in the fluid from passing the outlet tubing 50 to be dispensed into the blood vessels of a patient. The flared lower portion 23 is fastened in the trough 321.

The float valve 10 comprises a plunger 11, a fastening member 12, a lower float member 13, a block member 14, and an upper float member 15. The fastening member 12 comprises an inner cylinder 121 open to both ends, an annular outer member 1241, three equally spaced ribs 122 interconnecting the inner cylinder 121 and the outer member 1241 with a passageway 123 defined between any two adjacent ribs 122, and an externally extending annular flange 124 on the top mouth of the outer member 1241, the flange 124 being rested upon the mouth 311 and fastened by the inclined portion of the inner surface of the reservoir 21. The elongated plunger 11 is slidably disposed through the inner cylinder 121. The upper float member 15 comprises an outer cylindrical member 151 with a plurality of longitudinal grooves formed on its outer surface, and an inner cylindrical member 152 with one end of the plunger 11 fastened therein. The lower float member 13 comprises an outer cylinder 131, an inner cylinder 132 with the other end of the plunger 11 fastened therein, the inner cylinder 132 having a less elevation than that of the outer cylinder 131, an annular groove 1311 formed between the outer and inner cylinders 131 and 132 as fluid reservoir, and a hollow projection 133 extending downward from bottom of the lower float member 13. The projection 133 is in communication with the inner cylinder 132. The block member 14 comprises a top protrusion 141 having an enlarged head fastened in the narrow bottom opening of the projection 133, and an annular bottom skirt 142.

As shown in FIGS. 5 to 8, an IV infusion operation is described in detailed below. The skirt 142 is sealingly rested upon bottom of the inner cylinder 31 to block the opening (i.e., exit) 331 in an inoperative position (see FIGS. 6, 8). Next, attach the inlet tubing 40 to an IV fluid bag (not shown). Next, fluid L may pass the drip chamber 20 as it drips out of the inlet tube 22 via the inlet tubing 40. Fluid L may then enter the groove 1311 and the inner cylinder 31 via the passageways 123. Hence, both the upper and lower float members 15 and 11 are floated as fluid L is gradually stored in the inner cylinder 31. It is understood that the floating of both the upper and lower float members 15 and 13 is made possible because the plunger 11 may slide along the hollow of the inner cylinder 121. Fluid L may further flow into the outlet tubing 50 for dispensing into a patient via the opening 331 and the clamping connector 333 once the lower float member 13 moves upward to unblock the opening 331. Fluid L in the inner cylinder 31 is gradually accumulated because the rate of fluid flowing into the inner cylinder 31 is faster than the rate of fluid flowing out of the inner cylinder 31. The upward movement of both the upper and lower float members 15 and 11 will be stopped when the outer cylinder 131 contacts the ribs 122. At this position (see FIG. 5), the inner cylinder 31 and the groove 1311 are full of fluid L and fluid L may begin to accumulate in the inner cylinder 21. As such, the liquid level in the inner cylinder 21 is higher than the upper float member 15 (i.e., the upper float member 15 being submerged in fluid L). The sliding mechanism of the float valve 10 is thus also described. It is understood that both the upper and lower float members 15 and 13 may move up and down in the drip mechanism 100.

Fluid level in both the drip chamber 20 and the drip assembly 30 begins to fall once the fluid in the IV fluid bag is used up. Further, fluid L in the inner cylinder 31 may drop to its lowest level with the opening 331 being blocked (see FIGS. 6, 8). Advantageously, fluid L stored in the inner cylinder 131 can increase weight of the lower float member 13 so as to insure the sealing engagement of the skirt 142 with the bottom of the inner cylinder 31. The watertight blocking of the opening 331 also prevents blood from flowing back to the drip mechanism 100. The provision of the upper float member 15 can increase balance of the float valve 10 in sliding operation.

Figure 1:
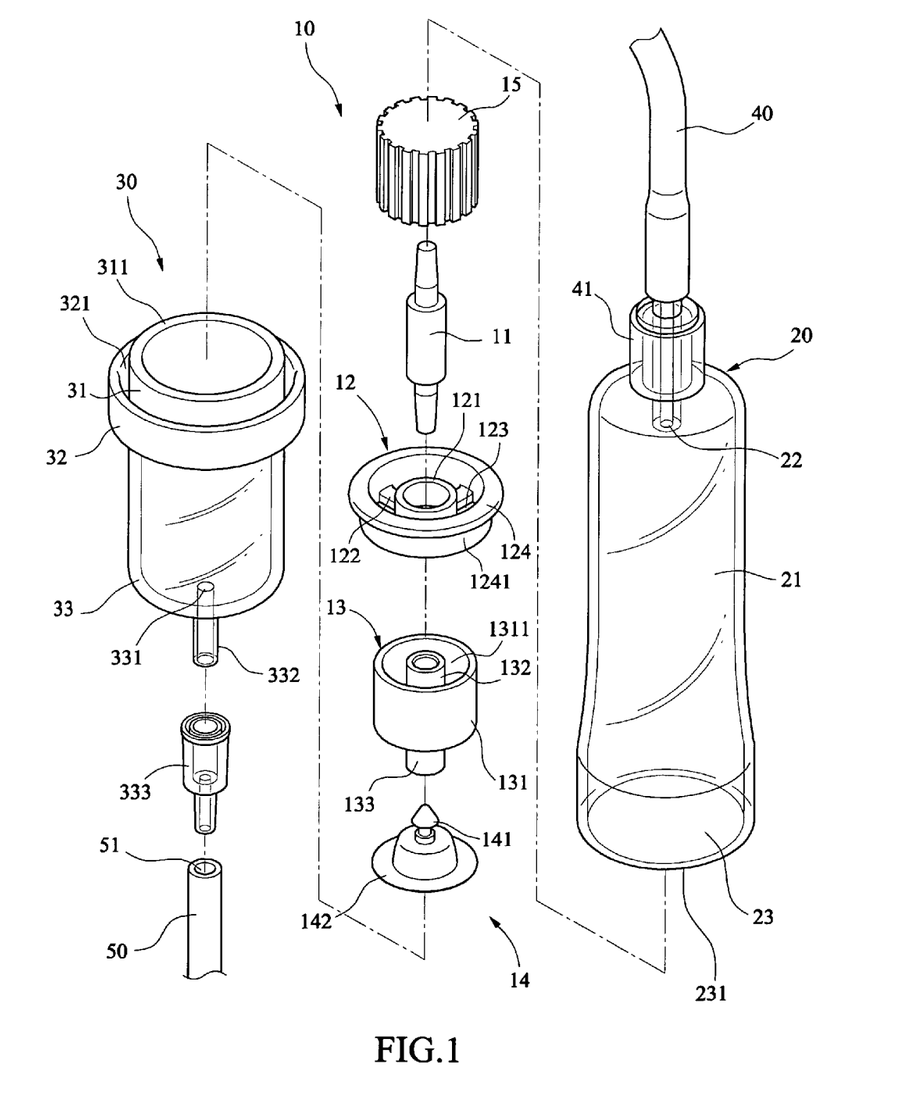
FIG. 1 is an exploded view of a first preferred embodiment of an automatic intravenous fluid flow control device according to the invention.
Figure 2:
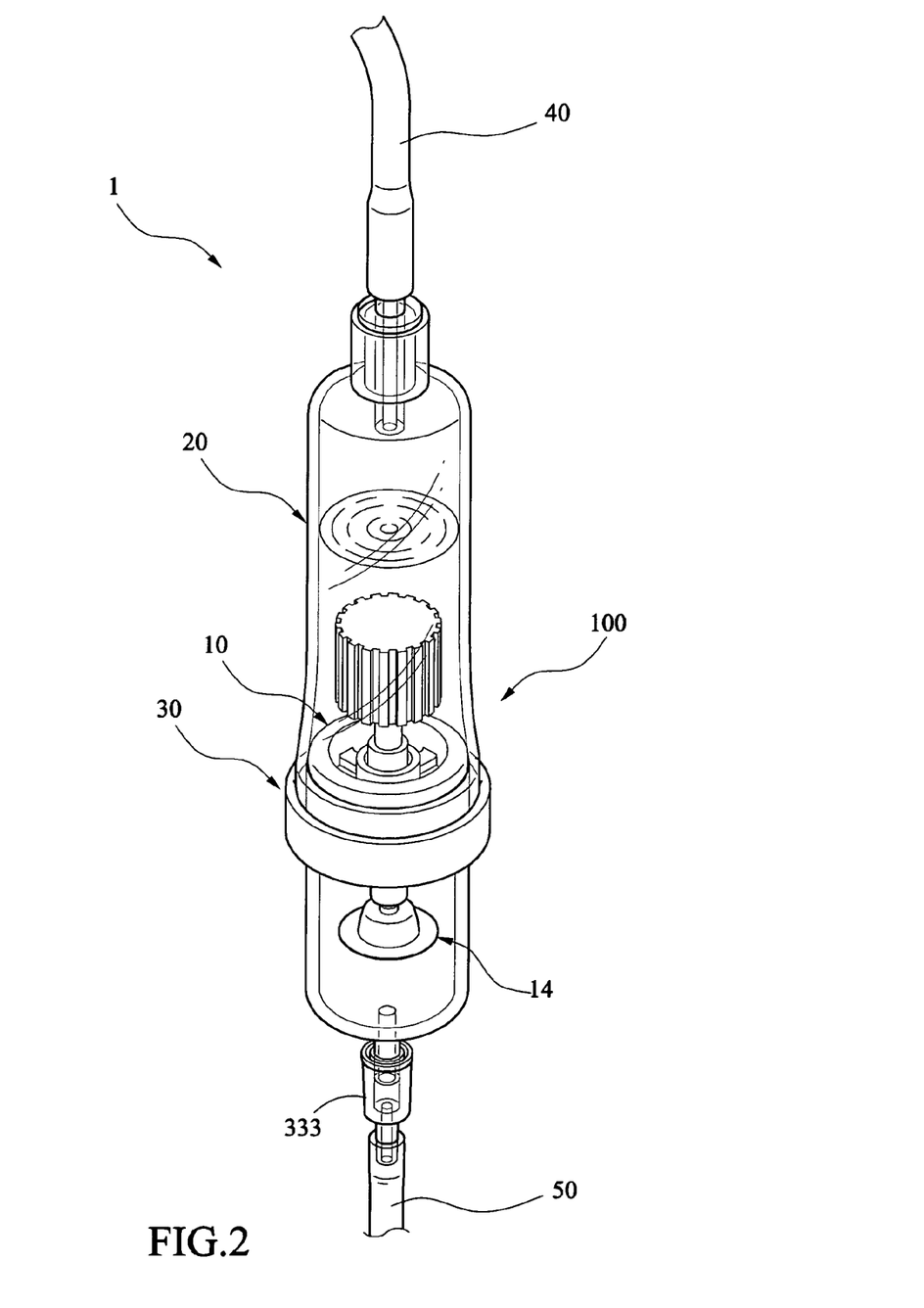
FIG. 2 is a perspective view of the assembled IV fluid flow control device.
Figure 3:
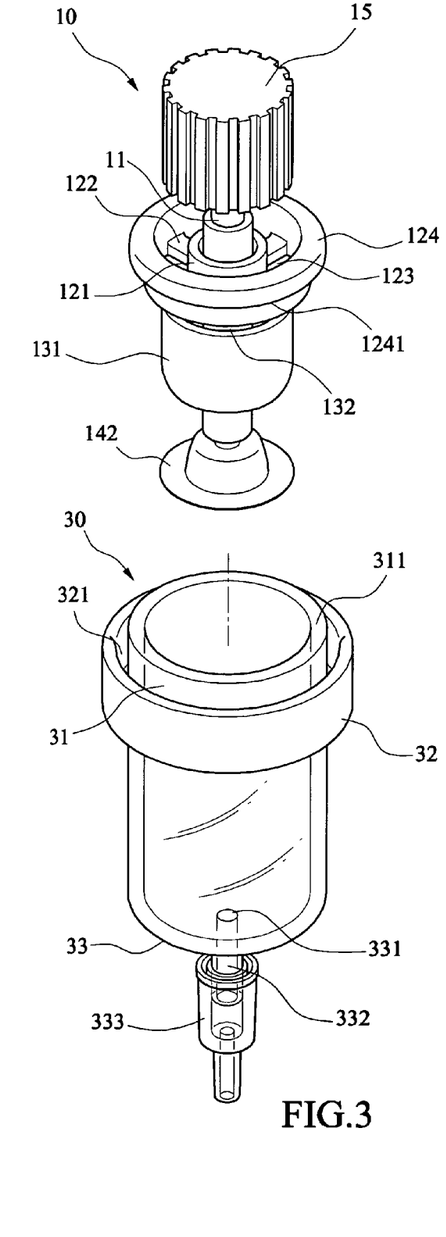
FIG. 3 is an exploded perspective view of the IV fluid flow control device.
Figure 3A:
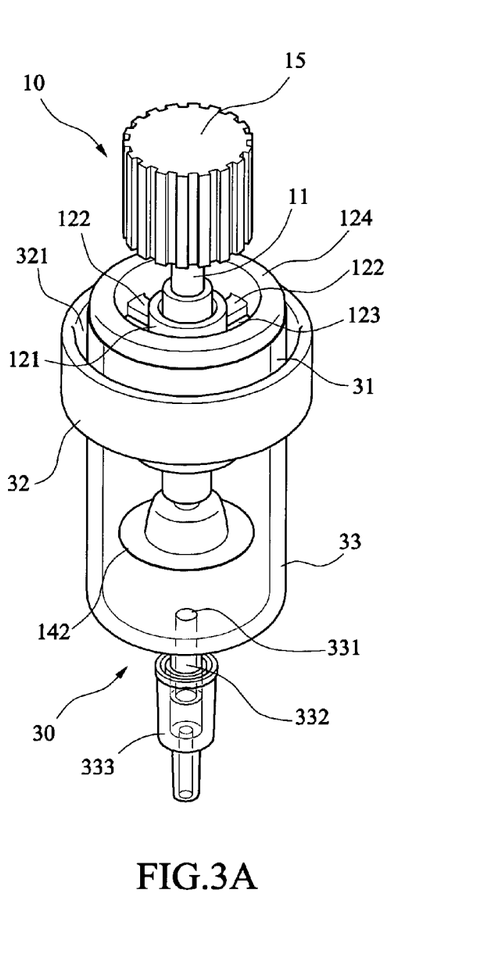
FIG. 3A is a perspective view of the assembled IV fluid flow control device of FIG. 3.
Figure 4:
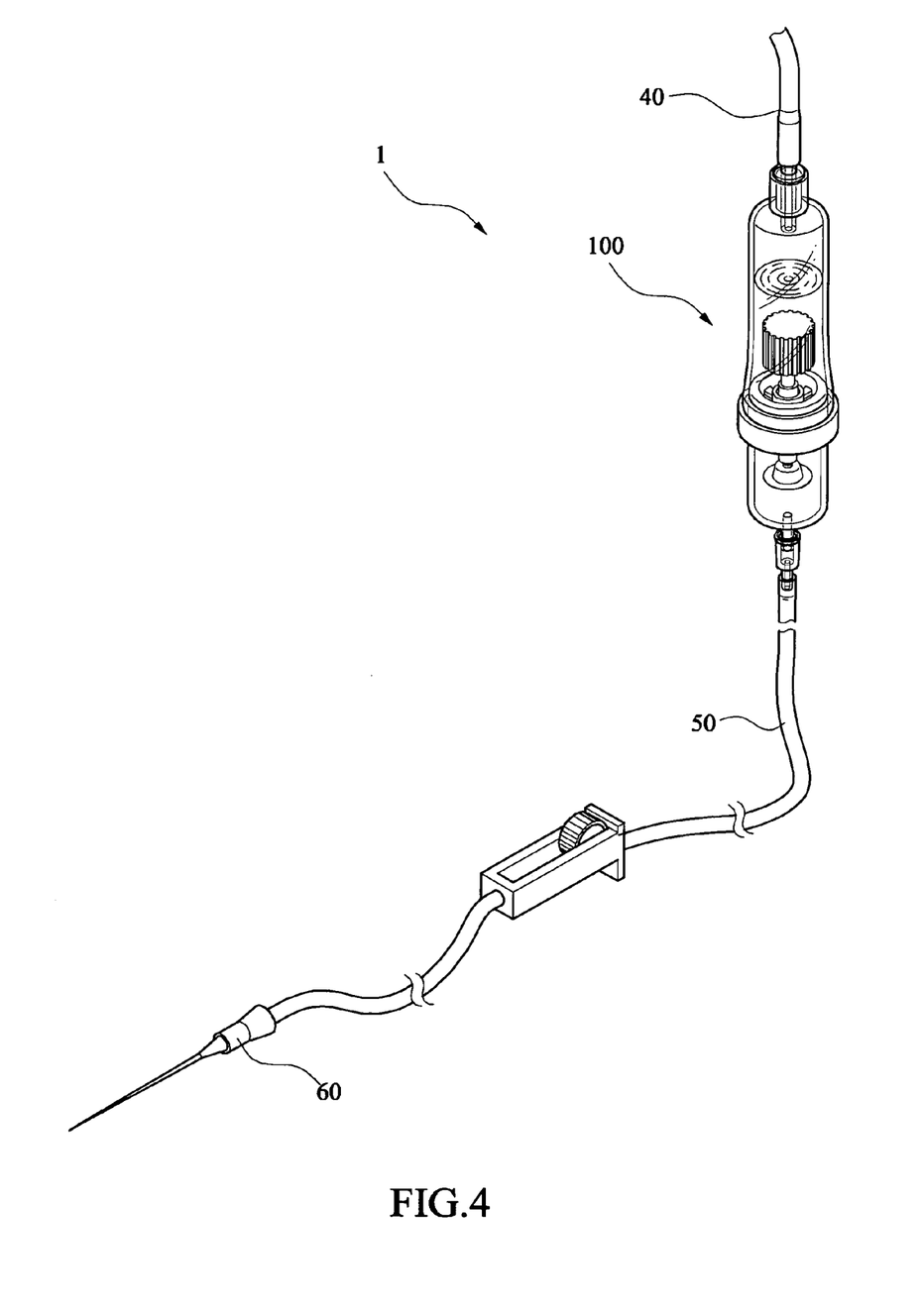
FIG. 4 is a perspective view of an IV infusion set incorporating the IV fluid flow control device of the invention in FIG. 2.
Figure 5:
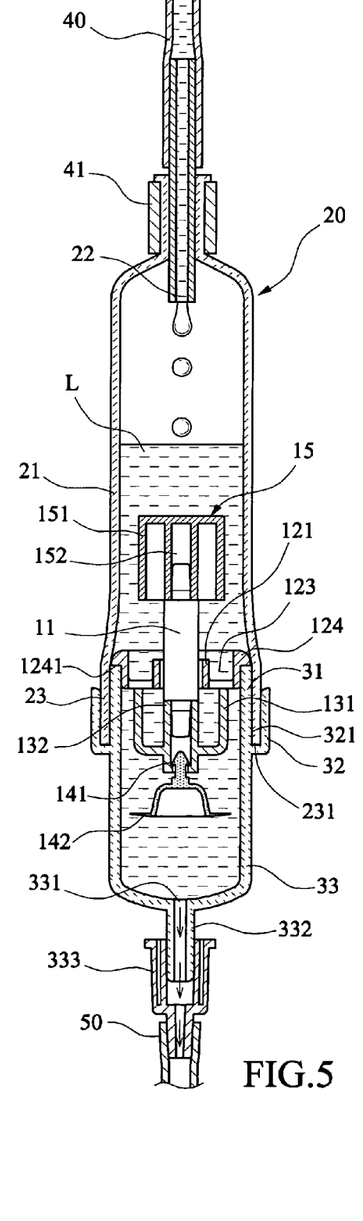
FIG. 5 is a longitudinal sectional view of the IV fluid flow control device of FIG. 2 where fluid is being dispensed.
Figure 6:
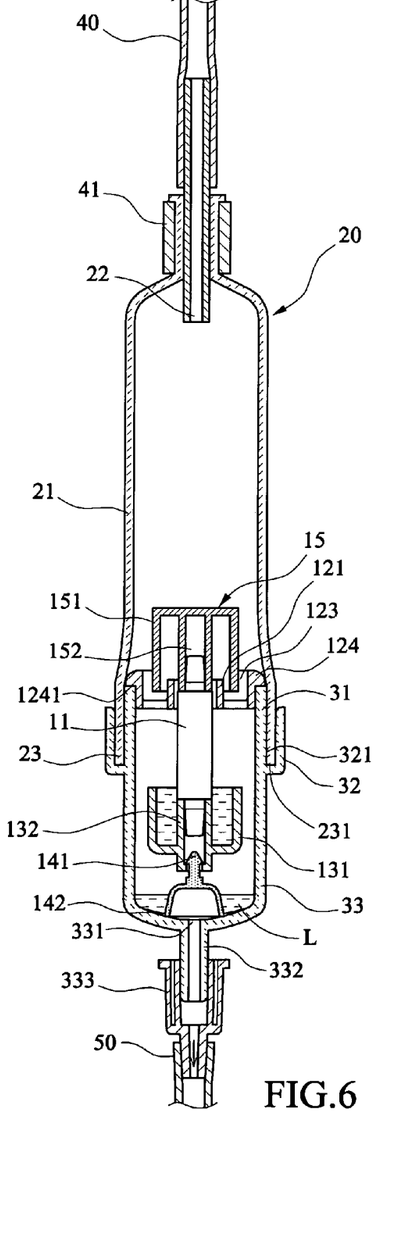
FIG. 6 is a view similar to FIG. 5 where the fluid in the IV fluid flow control device being substantially used up.
Figure 7:
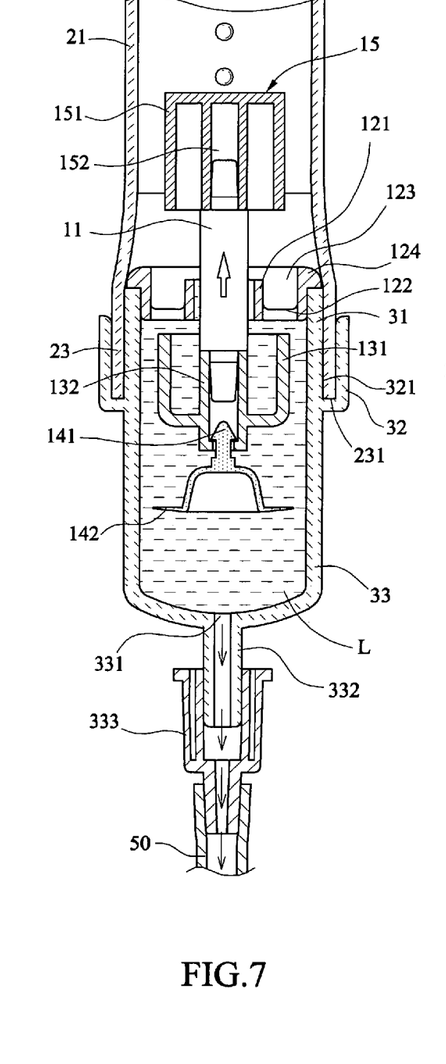
FIG. 7 is a fragmentary view of FIG. 5.
Figure 8:
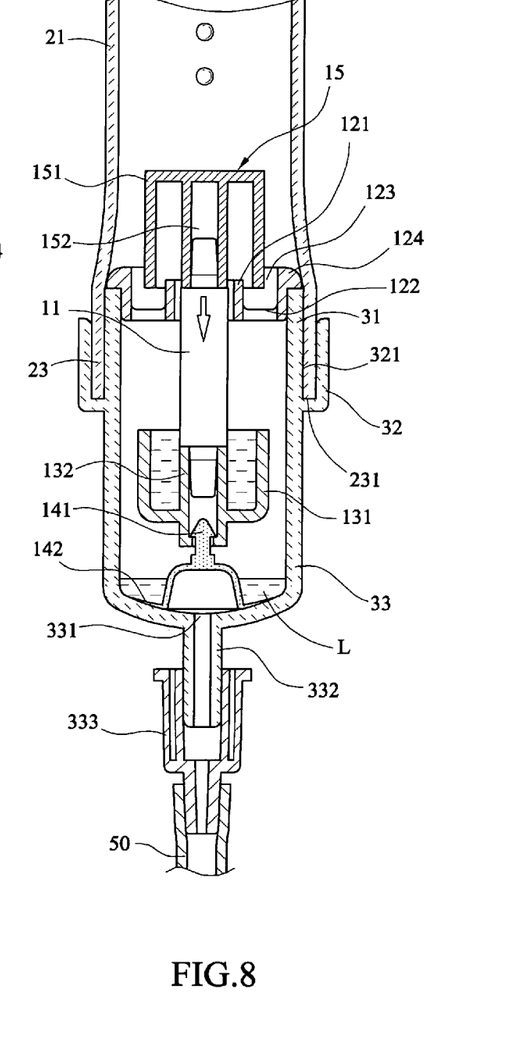
FIG. 8 is a fragmentary view of FIG. 6.
Figures 9, 9A:
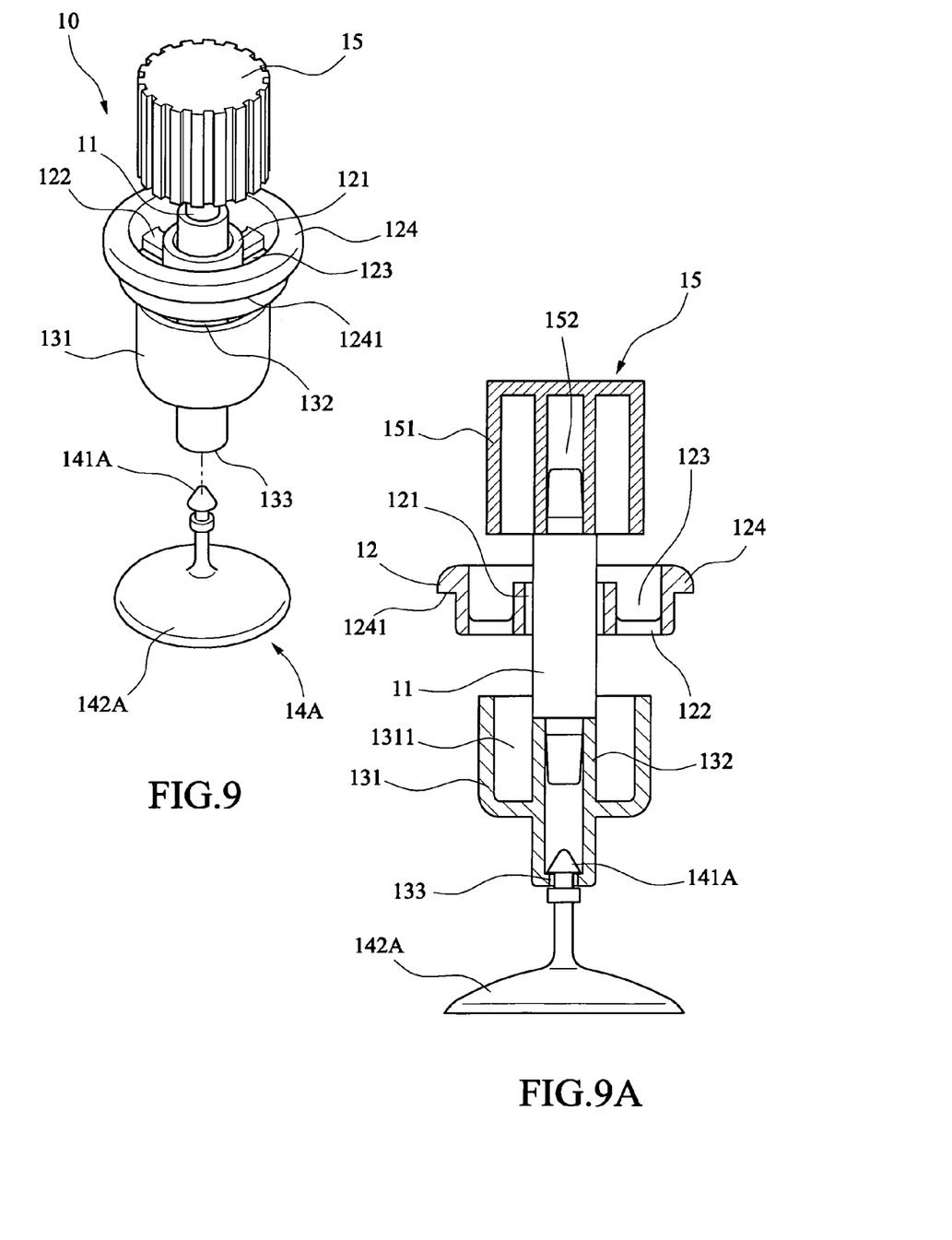
FIG. 9 is an exploded perspective view of a second preferred embodiment of float valve according to the invention different from the first preferred embodiment of the float valve shown in FIG. 1.
FIG. 9A is a longitudinal sectional view of the assembled float valve of FIG. 9.

Referring to FIGS. 9 and 9A, a second preferred embodiment of float valve 10 according to the invention different from the first preferred embodiment of the float valve in FIGS. 1 to 8 is shown. The characteristics of the second preferred embodiment of float valve 10 are detailed below. The block member 14A comprises a disc shaped base 142A and an enlarged head 141A fastened in the narrow bottom opening of the projection 133.

Figures 10, 10A:
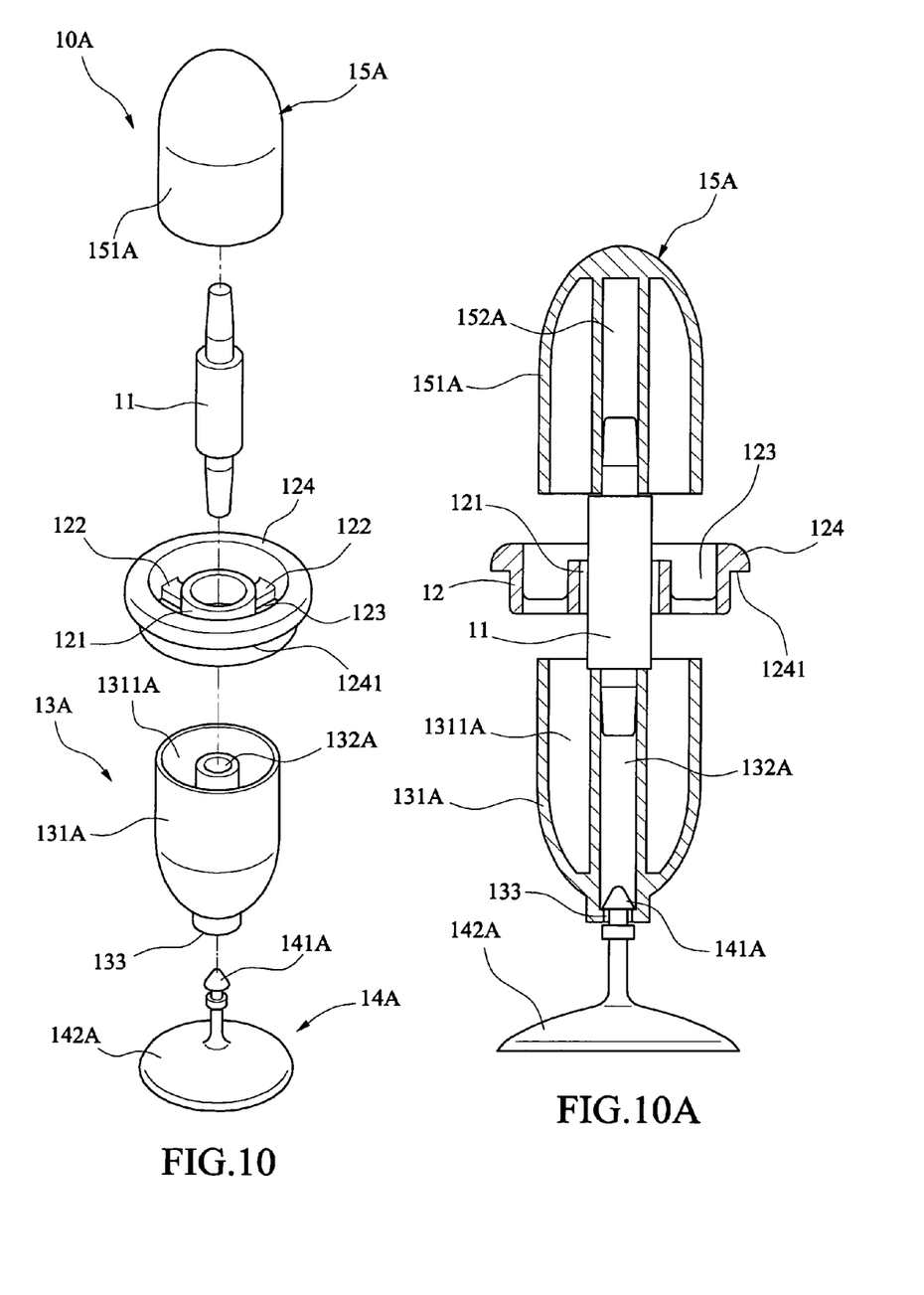
FIG. 10 is an exploded perspective view of a third preferred embodiment of float valve according to the invention.
FIG. 10A is a longitudinal sectional view of the assembled float valve of FIG. 10.

Referring to FIGS. 10 and 10A, a third preferred embodiment of float valve 10A according to the invention different from the first preferred embodiment of the float valve in FIGS. 1 to 8 is shown. The characteristics of the second preferred embodiment of float valve 10A are detailed below. The block member 14A comprises a disc shaped base 142A and an enlarged head 141A fastened in the narrow bottom opening of the projection 133. The lower float member 13A is shaped as a bullet. The upper float member 15A is also shaped as a bullet.

Figure 11:
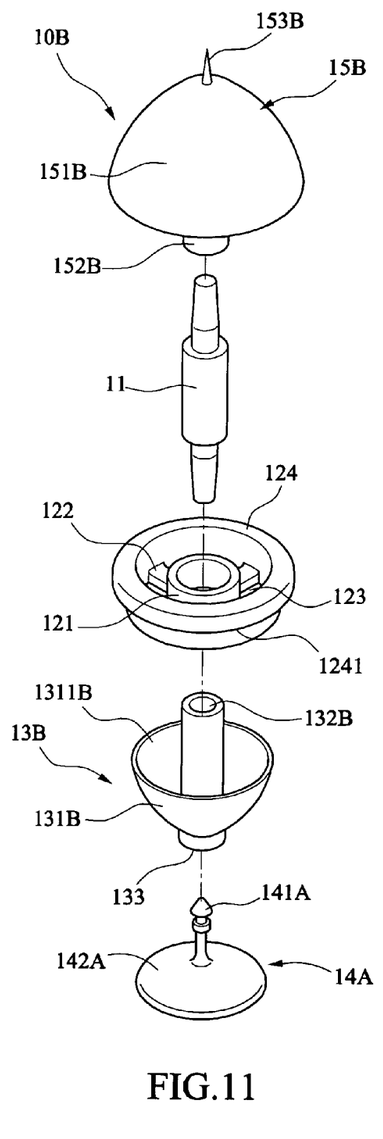
FIG. 11 is an exploded perspective view of a fourth preferred embodiment of float valve according to the invention.
Figure 11A:
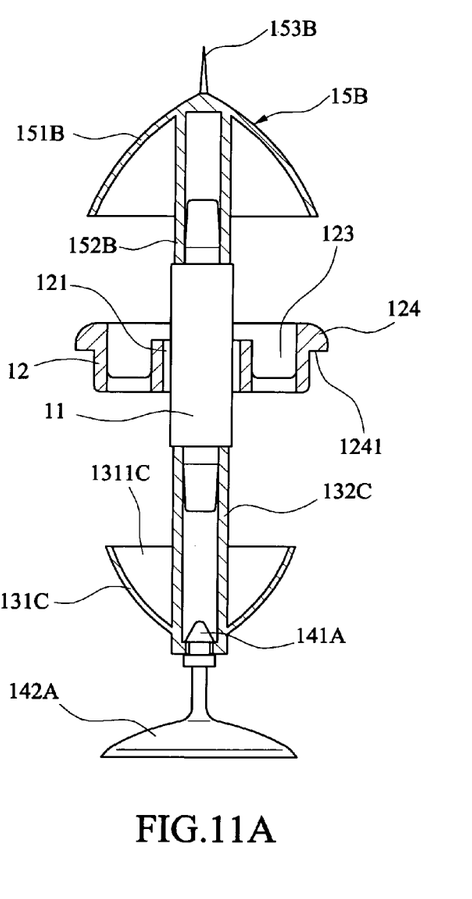
FIG. 11A is a longitudinal sectional view of the assembled float valve of FIG. 11.

Referring to FIGS. 11 and 11A, a fourth preferred embodiment of float valve 10B according to the invention different from the first preferred embodiment of the float valve in FIGS. 1 to 8 is shown. The characteristics of the second preferred embodiment of float valve 10B are detailed below. The block member 14A comprises a disc shaped base 142A and an enlarged head 141A fastened in the narrow bottom opening of the projection 133. The lower float member 13B is shaped as a bowl. The upper float member 15B is also shaped as an inverted blow and further has a cone 153B projecting out of a top center. The cone 153B aims at piercing bubbles of gas in the fluid so as to increase the number of bubbles of gas flowing to a lower portion of the upper float member 15B and beyond.

Figure 12:
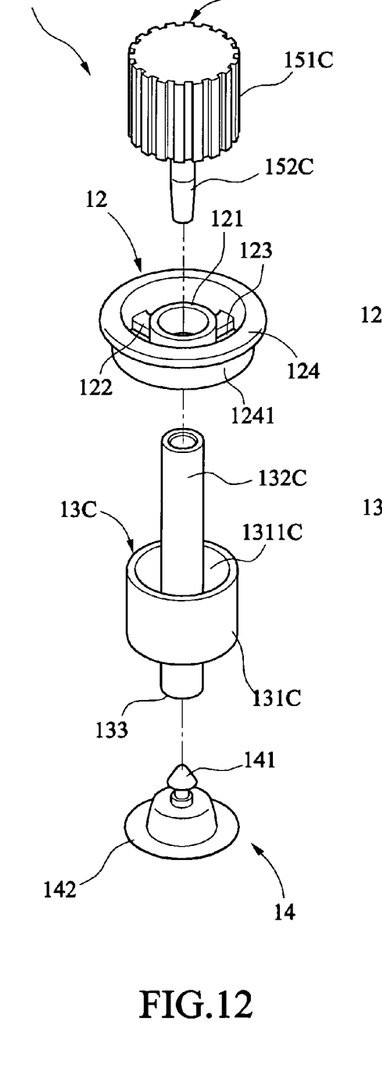
FIG. 12 is an exploded perspective view of a fifth preferred embodiment of float valve according to the invention.
Figure 12A:
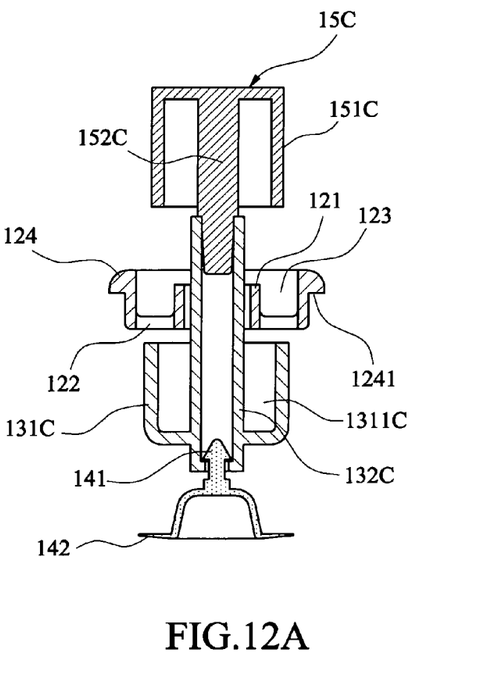
FIG. 12A is a longitudinal sectional view of the assembled float valve of FIG. 12.

Referring to FIGS. 12 and 12A, a fifth preferred embodiment of float valve 10C according to the invention different from the first preferred embodiment of the float valve in FIGS. 1 to 8 is shown. The characteristics of the second preferred embodiment of float valve 10C are detailed below. The plunger is eliminated and its function is replaced by the inner cylinder 132C which is further elongated to slidably pass through the inner cylinder 121. Further, the inner cylindrical member 152C is not hollow so as to insert into the inner cylinder 132C for fastening.

Figure 13:
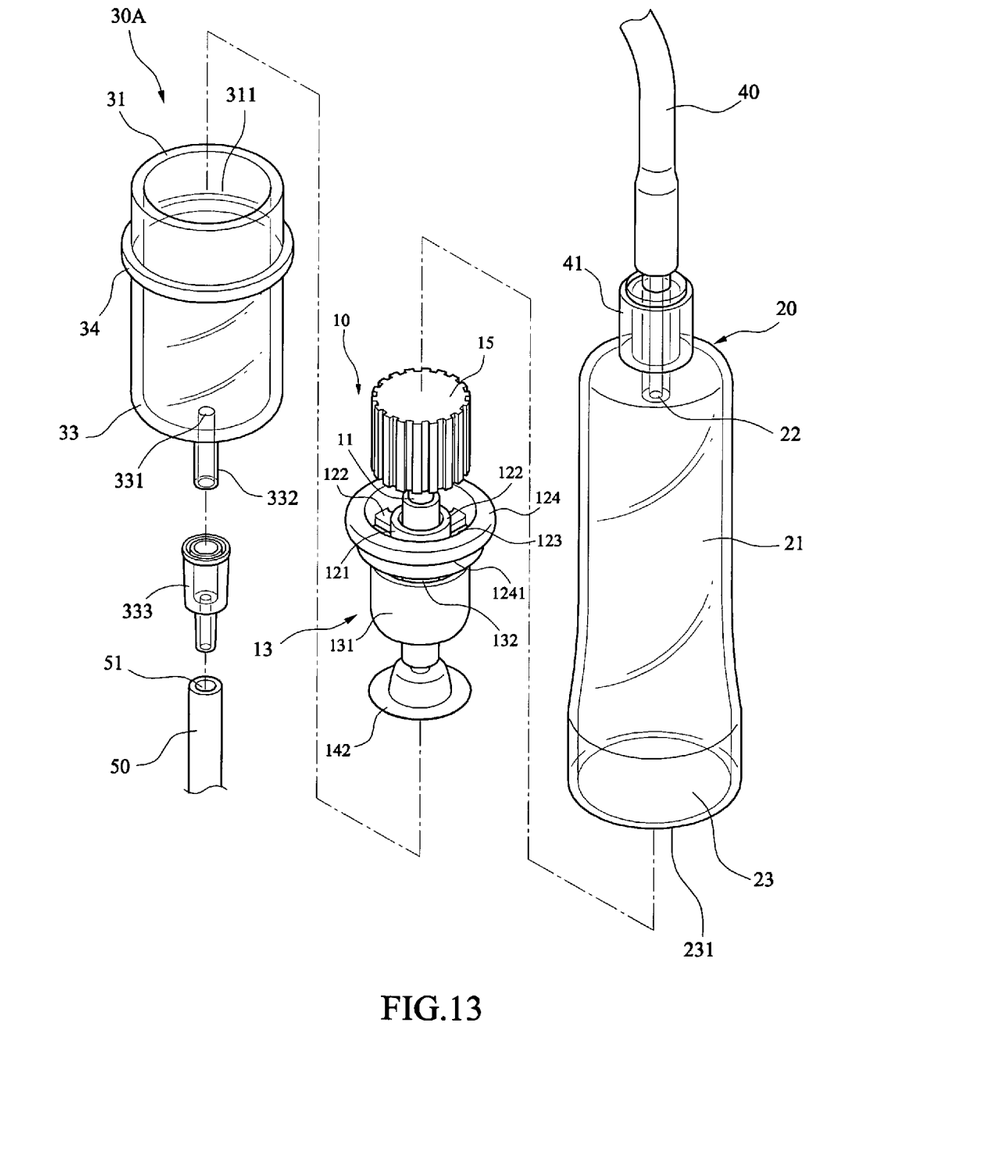
FIG. 13 is an exploded view of a second preferred embodiment of an automatic intravenous fluid flow control device according to the invention.
Figure 14:
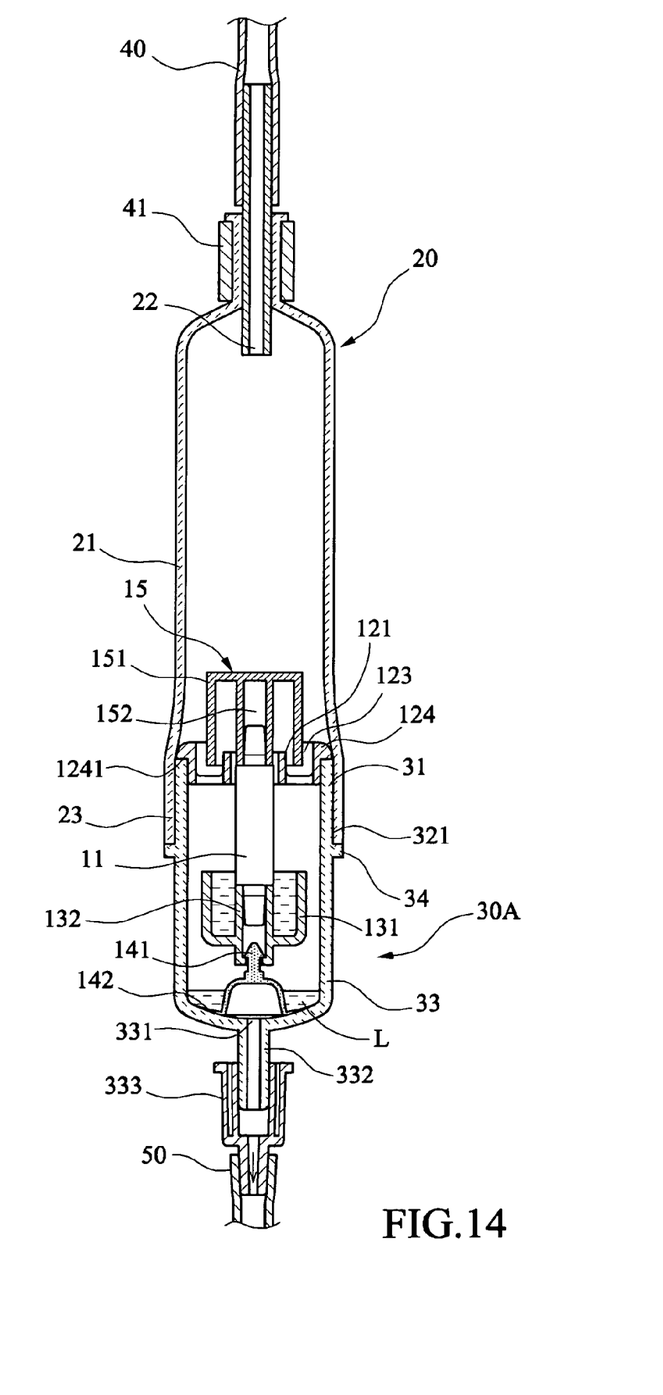
FIG. 14 is a longitudinal sectional view of the assembled intravenous fluid flow control device shown in FIG. 13.

Referring to FIGS. 13 and 14, an automatic IV fluid flow control device in accordance with a second preferred embodiment of the invention is shown. The characteristics of the second preferred embodiment of automatic IV fluid flow control device are detailed below. The outer cylinder is replaced with an annular flange 34 on the periphery of the inner cylinder 31. The bottom 231 is securely rested upon the flange 34 because the flared lower portion 23 is secured onto the inner cylinder 31.

While the invention has been described in terms of preferred embodiments, those skilled in the art will recognize that the invention can be practiced with modifications within the spirit and scope of the appended claims.

What is claimed is:

1. An intravenous fluid flow control device comprising:
a flexible drip chamber (20) comprising a fluid entrance (22) and an open bottom (231);
a rigid drip assembly (30) secured to the drip chamber (20) and comprising an inner cylinder (31) having a bottom exit (331); and
a float valve (10) disposed within both the drip chamber (20) and the drip assembly (30), the float valve (10) comprising a fastening member (12) fastened in a joininq portion of the drip chamber (20) and the drip assembly (30), the fastening member (12) including a hollow inner cylinder (121), an elongated plunger (11) slidably disposed through the inner cylinder (121), an upper float member (15) secured to one end of the plunger (11), a lower float member (13) secured to the other end of the plunger (11), and a block member (14) secured to the lower float member (13), the block member (14) being for sealingly blocking the exit (331) when the control device is in an inoperative position,
wherein fluid flows though the drip chamber (20) and the fastening member (12) into the inner cylinder (31) for accumulation so as to float the block member (14), thereby unblocking the exit (331) and moving the plunger (11) upward when the control device is in an operative position;
wherein the drip assembly (30) further comprises an annular outer member (32) depending upward from a periphery of the inner cylinder (31) to define an annular trough (321) therebetween for fastening the drip chamber (20) therein;
wherein the fastening member (12) further comprises an annular outer member (1241), a plurality of spaced ribs (122) interconnecting the inner cylinder (121) and the outer member (1241) with a passageway (123) defined between any two adjacent ribs (122), and an externally extending annular flange (124) on one end of the outer member (1241), the flange (124) being securely rested upon one end of the inner cylinder (31); and
wherein the lower float member (13) comprises an outer cylinder (131), an inner cylinder (132) with the other end of the plunger (11) fastened therein, the inner cylinder (132) having a lesser elevation than that of the outer cylinder (131), an annular groove (1311) formed between the outer and inner cylinders (131, 132) as a fluid reservoir, and a hollow bottom projection (133), and wherein the upward movement of the plunger (11) is stopped when the outer cylinder (131) contacts the ribs (122).

2. The intravenous fluid flow control device of claim 1, wherein the block member (14) comprises a top protrusion (141) fastened in the projection (133).

* * * * *